United States Patent [19]
Pitaru et al.

[11] Patent Number: 5,955,438
[45] Date of Patent: Sep. 21, 1999

[54] COLLAGEN-BASED MATRIX

[75] Inventors: Sandu Pitaru, Tel-Aviv; Matityahu Noff, Rehovot, both of Israel

[73] Assignee: ColBar R & D Ltd., Ramat-Hasharon, Israel

[21] Appl. No.: 08/504,364

[22] Filed: Jul. 19, 1995

[30] Foreign Application Priority Data

Jul. 19, 1994 [IL] Israel .......................................... 110367

[51] Int. Cl.$^6$ ........................... A61K 47/42; C07K 1/107
[52] U.S. Cl. ........................... 514/21; 514/774; 435/273; 524/22; 530/356; 424/435
[58] Field of Search ............... 514/21, 772, 774, 514/801; 435/273; 524/22; 530/356; 424/435

[56] References Cited

U.S. PATENT DOCUMENTS

| | | | |
|---|---|---|---|
| 4,971,954 | 11/1990 | Brodsky et al. | 514/21 |
| 5,700,479 | 12/1997 | Lundgren et al. | 424/435 |

FOREIGN PATENT DOCUMENTS

| | | |
|---|---|---|
| 0693523 | 1/1996 | European Pat. Off. . |
| 2 679 778 | 2/1993 | France . |
| 43 02 708 A1 | 8/1994 | Germany . |

OTHER PUBLICATIONS

Pachence (1996) J. BioMed. Mat. Res. 33: 35–40.
R.R. Kohn et al; Collagen Again In Vitro By Nonenzymatic Glycosylation And Browning; Diabetes, vol. 33, Jan. 1984; pp. 57–59.
M. J. C. Kent et al; Evidence For Glucose–Mediated Covalent Cross–Linking Of Collagen After Glycosylation In Vitro; Biochem. J; vol. 225; pp. 745–752; 1985.

*Primary Examiner*—Lila Feise
*Assistant Examiner*—Michael Pak
*Attorney, Agent, or Firm*—Browdy and Neimark

[57] ABSTRACT

A collagen matrix comprise collagen fibrils which are cross-linked to one another by a reducing sugar or a reducing sugar derivative. The collagen matrix may be formed into a membrane useful in guided tissue regeneration.

20 Claims, 1 Drawing Sheet

COLLAGEN-BASED MATRIX

FIELD OF THE INVENTION

The present invention concerns a novel collagen-based matrix and devices comprising this matrix. A particular example of such device is a collagen-based sheet useful in a guided tissue regeneration (GTR), which will be referred to herein as "GTR membrane".

A particular application of the GTR membrane of the invention is in dentistry, for guided tissue regeneration of periodontal tissue.

The present invention also concerns a process for the preparation of the matrix.

BACKGROUND OF THE INVENTION

Guided tissue regeneration is a surgical procedure intended to restore or regenerate the morphology and function of tissues or organs that were destroyed by disease or trauma. In tissue regeneration, the regenerating tissues have to repopulate the same site and space previously occupied by the healthy tissues that were destroyed. Furthermore, to restore the morphological and functional relationships between the different regeneration tissues at the regeneration site, the repopulation of the affected site and the subsequent differentiation of the repopulating cells should be an orderly and concerted process.

The technique of GTR aims to allow orderly and concerted repopulation of an affected site by regenerating tissues. To this end, a barrier is interposed between the regenerating tissues and the tissue that might intervene with the regenerative process. The barrier is maintained in place until the affected site is repopulated by the proper tissues and the regenerating tissues reach maturity.

Membrane barriers are currently used mainly in dentistry, for GTR of regenerating periodontal tissues that were destroyed by periodontal disease or trauma. Generally, two types of membranes are in use, membranes made of non-degradable material and membranes made of degradable materials.

Collagen are a family of proteins with a well determined triple helical configuration. Among these proteins, collagen Type I is most prevalent, constituting approximately 25% of the body's proteins and 80% of the connective tissues' proteins. Collagen Type I polymerizes to form aggregates of fibers and bundles. Collagen are continuously remodeled in the body by degradation and synthesis. Collagen Type I is degraded only by a specific enzyme—collagenase, and is resistant to any non-specific proteolytic degradation.

Collagen is a weak antigen and most of its antigenicity resides in the non-helical terminals of the molecule. These terminals may be removed by enzymes such as pepsin. Its weak antigenicity and its relative resistance to degradation make collagen a good candidate as a building material of implantable devices.

A molecular solution of type I collagen can be prepared from a connective tissue rich in this protein and the molecular collagen can then be reassembled into fibrils which can then combine to form a collagen matrix. Collagen matrices can be molded in vitro into numerous implantable devices such as, for example collagen sheets, collagen tubes, etc.

When used to form implantable devices, collagen matrices should maintain their integrity for long periods of time. The resistance towards degradation of the collagen fibrils can be increased by increasing the number of intermolecular cross-links. Several agents, such as aldehyde fixatives and imides, and treatments such as radiations have been used to achieve this purpose. The main drawbacks of such treatments are toxicity and inability to accurately control the degree of cross-linking.

SUMMARY OF THE INVENTION

It is the object of the present invention to provide a collagen matrix suitable for use in implantable devices such as membranes or tubes for guided tissue regeneration.

It is furthermore the object of the present invention to provide a process for the preparation of such a matrix.

It is still further the object of the present invention to provide a kit comprising ingredients useful in guided tissue regeneration procedures.

It is still further the object of the present invention to provide a method of guided tissue regeneration (GTR).

It is still further an object to provide space maintainers for use in GTR procedures.

It was found in accordance with the invention, that collagen can be rendered resistant to a collagenolytic degradation by means of cross-linking the collagens by reacting it with a reducing sugar. Thus, in accordance with the present invention a cross-linked collagen matrix is provided which can be maintained substantially intact within the body for long periods of time and is thus useful as a building material of various collagen-based implantable devices.

The present invention provides, in accordance with a first of its aspects, a collagen matrix comprising collagen fibrils, the molecules or microfibrils of which are being cross-linked to one another by a cross-linking agent, the cross-linking agent comprising a reducing sugar, or a reducing sugar derivative.

The present invention further provides a process for preparing a collagen matrix comprising reacting collagen with a reducing agent whereby fibrils of the collagen become cross-linked to one another. Preferably, following preparation, the collagen matrix is dehydrated, e.g. in alcohol solution, and then subjected to critical point drying.

Said cross-linking agent may be an aldehyde mono sugar or a mono sugar derivative wherein the α-carbon exists in an aldehyde or ketone state in an aqueous solution.

Said cross-linking agent may be a compound represented by one of the following formulae I or II:

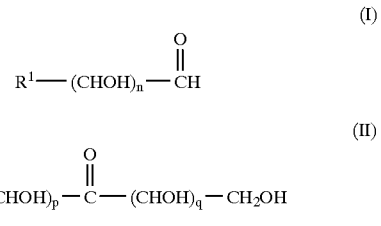

wherein:

R¹ is H or lower alkyl or alkylene, an amino acid, a peptide, a saccharide, purine or pyrimidine base, a phosphorylated purine or pyrimide base;

n is an integer between 2–9, and p and q are each independently an integer between 0–8, provided that p and q together are at least 2 and not more than 8.

A reducing sugar can form a Schiff base with an α or ε amino groups of amino acids of the collagen molecule. The Schiff base undergoes an Amadori Rearrangement to form a ketoamine product by the following reaction scheme:

a. Aldehyde sugar

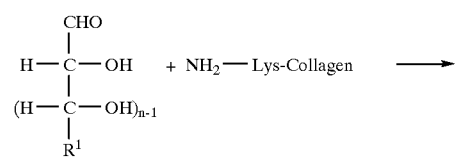

Reducing Sugar

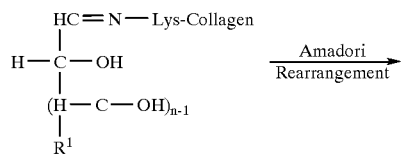

Schiff base formation

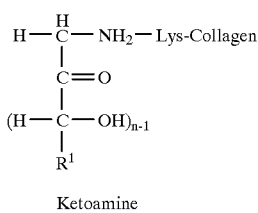

Ketoamine b. Ketone sugar

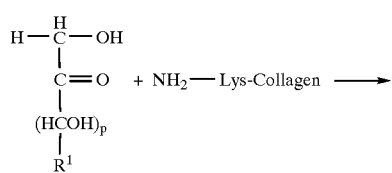

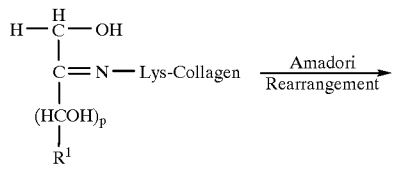

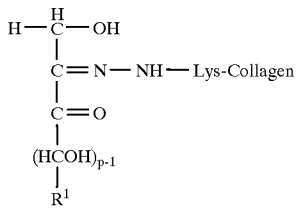

Two adjacent ketoamine groups can then condense to form a stable intermolecular or intramolecular crosslink.

When the cross-linking agent is ribose, a stable cross-linked via a pertosidine group may be formed by the following reaction scheme (in the following scheme "A" denotes a first collagen molecule and "B" a second collagen molecule):

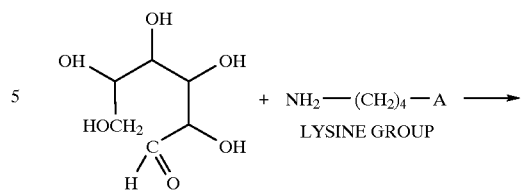

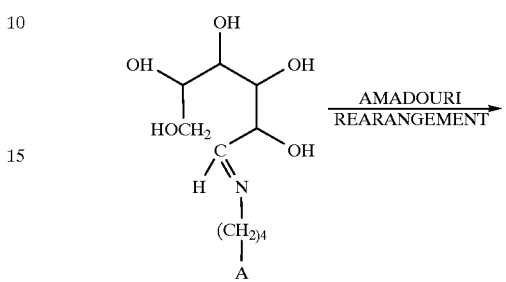

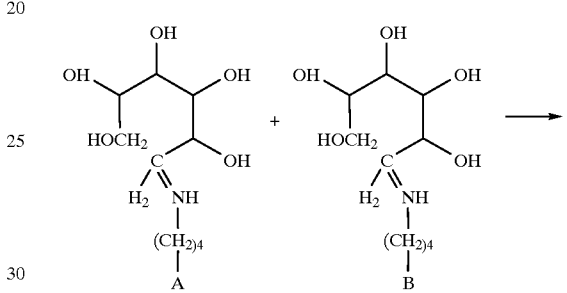

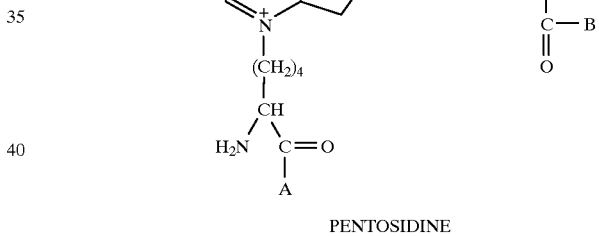

PENTOSIDINE

Examples of said reducing agent are glycerose, threose, erythrose, lyxose, xylose, arabinose, ribose, allose, altrose, glucose, mannose, gulose, idose, galactose, talose, or any other diose, triose, tetrose, pentose, hexose, septose, octose, nanose or decose.

The degradation rate of the collagen matrix when in situ can be controlled by the extent of cross-linking between the collagen molecules in the matrix. This may in turn be controlled by the concentration of the sugar during the preparation of the matrix, the temperature, and the extent of time during which the collagen is exposed to the sugar.

The matrix may comprise also various agents having a certain therapeutic effect which are immobilized within the matrix by said sugars. When the matrix is in situ, these agents are gradually released during the gradual degradation of the matrix. These agents include antimicrobial agents, anti-inflammatory agents, factors having tissue regeneration induction properties, etc.

Examples of antimicrobial agents are antibiotics such as penicillin, cefalosporins, tetracyclines, streptomycin, gentamicin; sulfonamides; and antifungal drugs such as myconazolle.

Examples of anti-inflammatory agents are cortisone, a synthetic derivative thereof, or any synthetic anti-inflammatory drugs.

Examples of factors having tissue inductive properties are growth factors such as fibroblast growth factor, platelet derived growth factors, transforming growth factors, cementum growth factors, insulin-like growth factors, etc.; differentiating factors such as bone morphogenetic proteins; attachment factors (these can also be linked to the matrix by means of cross-linkings by the sugars or by taking advantage of their natural capacity to bind to collagen).

The collagen matrix of the invention is useful for the preparation of a number of implantable devices including sheets serving as membrane barriers for GTR, collagen-based tubes, for nerve or vascular regeneration, etc.

The barrier membranes of the invention typically have a thickness ranging from 0.05 mm to 2 mm. The size of the membranes will range from about 0.5 $cm^2$ to 400 $cm^2$ or even more.

The collagen membranes of the invention are resistant to any non-specific proteolytic degradation. They are degraded by collagenase at a rate that can be controlled by the amount of cross-linking, as already pointed out above.

In accordance with one embodiment of the invention, the collagen matrix may be used in conjunction with a space-maintaining material ("space maintainer"). A space maintainer is used in some procedures in order to maintain a space in which the regenerating cells can migrate and repopulate. In some cases, such a space occurs naturally, as for example when a tumor is excised from a bone. In other cases such a space is not available, as for example in various types of periodontal or bone lesions. In such cases it is necessary to insert filling material between the barrier and the regenerating tissues. Examples of space maintainers are (i) hyaluronan (hyaluronic acid), (ii) mineralized freeze dried bone, (iii) deproteinazed bone, (iv) synthetic hydroxyapatite, (v) crystalline materials other than those mentioned under (ii)–(iv), enriched with osteocalcine or vitronectin, and (vi) heat-treated demineralized bone (the bone derived substance under (ii), (iii) and (vi) are preferably of human origin). Also possible are combinations of any of the above space maintainers, particularly hyaluronan and with one or more of the other space maintainers.

Hyaluronan, which is preferably provided a priori in a lyophilized form, is a polysaccharide consisting of repeating units of glucuronic acid and N-acetylglucoseamine. It has a molecular weight ranging from a few thousand to several million daltons, depending on the source of its extraction. Hyaluronan is naturally expressed in developing and healing tissues and has the capacity to bind large amounts of water. These properties allow the hyaluronan to be used as a space maintainer in combination with the membranes of the invention in GTR.

The use of mineralized bone, deproteinazed bone (which is natural hydroxyapatite prepared by ashing bone at 700° C.) or synthetic hydroxyapatite in combination with osteocalcine and vitronectin [osteocalcine is a bone protein, which is bound to hydroxyapatite (the mineral component of the bone) and which is believed to attract osteoclast (bone resorbing cells) to mineralized surfaces; vitronectin is an attachment protein and facilitates osteoclast attachment to mineralized bone surfaces] is novel and is believed to enhance the recruitment of osteoclast at the healing site. This in turn, enhances the resorption of these space-maintainers and facilitates their replacement by regenerating tissues.

Heat treatment of demineralized bone (e.g. freeze-dried) will denaturate the collagenous component of the bone matrix and allows for non-specific proteinazes to degrade the bone matrix. This in turn, enhances the degradation of the space maintainer and facilitates its replacement by regenerating tissues. Such a heat-treated preparation, particularly for this use is novel.

For various applications depending on the size, form and location of the regenerating site, the space maintainers may be enriched with one or more of the antibacterial, anti-inflammatory and tissue-inductive factors mentioned above; and/or enriched with a substance intended to aid in maintaining the shape of the space maintainer matrix, e.g. one or more matrix proteins selected from the group consisting of collagen, fibrin, fibronectin, osteonectin, osteopontin, tenascin, thrombospondin; and/or glycoseaminoglycans including heparin sulfate, dermatan sulfates, chondrointin sulfates, keratan sulfates, and many others.

These, provided by the present invention are the above novel space maintainers.

The present invention also provides a kit for use in GTR comprising the collagen membrane of the invention. In accordance with an embodiment of the invention, the kit comprises also a space maintainer. The collagen membrane as well as the hyaluronan may comprise one or more of the additives mentioned above.

In the following, the invention will be further illustrated by a description of specific embodiments and by examples describing some experiments performed within the framework of the invention, with reference made also to the annexed drawing.

DETAILED DESCRIPTION OF SPECIFIC EMBODIMENTS

Production of Collagen Membranes

Figure 1:
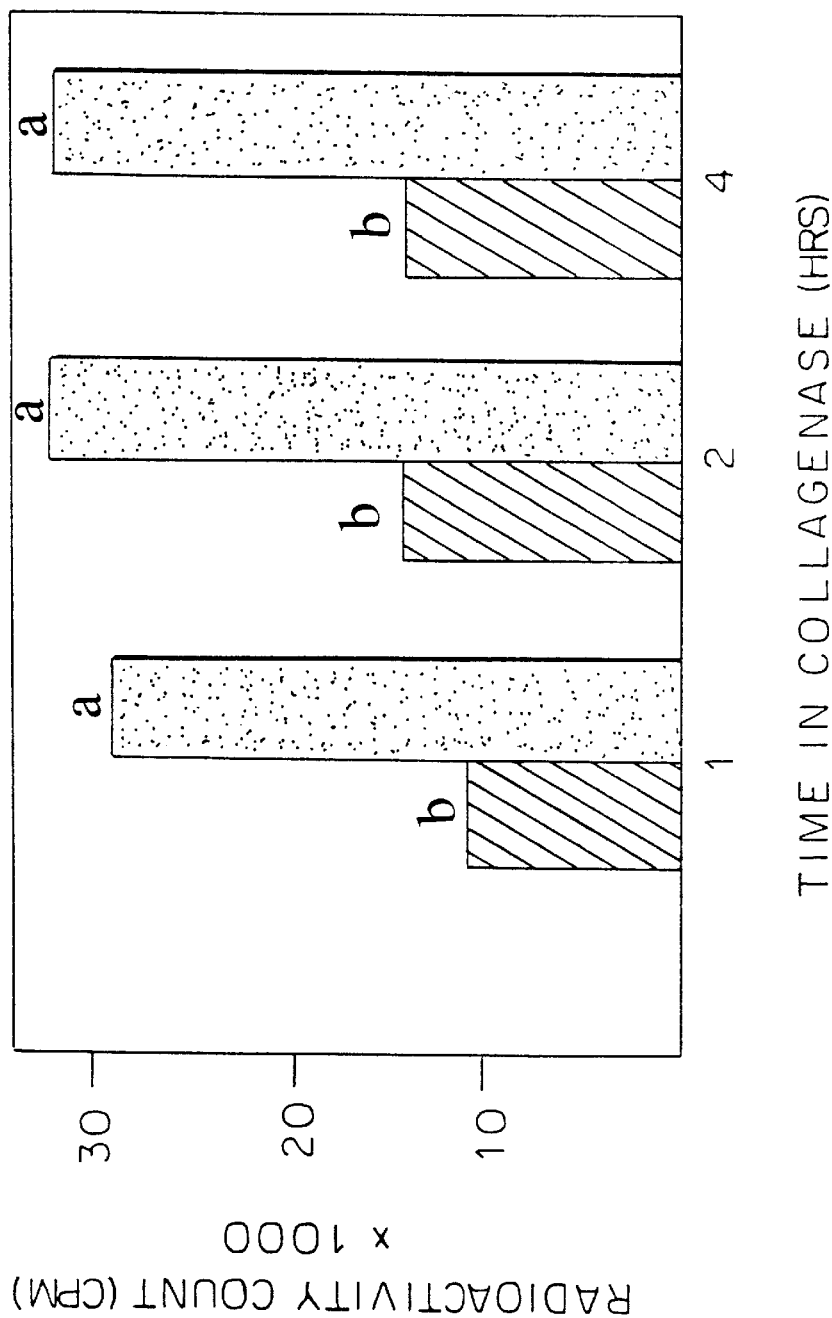
FIG. 1 shows results of an experiment in which radioactivity remaining of a tritium-labelled collagen matrix following degradation by collagenase, was measured. Collagen fibrils labelled with tritium were incubated in a solution comprising ribose in PBS (a) or in a PBS solution without ribose (b) for periods of time ranging for 1–16 days. Following this incubation the formed collagen matrix was treated with collagenase for 1 hour. The amount of radioactivity which remained in the matrix as percentage of the total, following the collagenase treatment is shown in the graph in the Figure. Matrices incubated in ribose for 9 days and longer were essentially resistant to collagen degradation.

Type I collagen may be obtained from bovine skin, tendon, placenta, or human placenta, by pepsinization as known per se. A molecular solution of purified pepsinized type I collagen (1–10 mg/ml) is dissolved in 0.05 M acetic acid and maintained at 4° C. is mixed with 0.1 M NaOH and then poured into an appropriate mold and incubated for 24 hours at a temperature ranging between 20–37° C. The matrix which is produced is then compressed by a piston which squeezes out the water until the required thickness of a membrane is obtained. The membrane is then incubated in a solution of ribose (having a concentration in the range of 0.05 M to 1 M for a period of time varying between 6 hours to 24 days, or sometimes even more, depending on the required resistance of the membrane to enzymatic degradation.

If desired, the ribose solution can be enriched by agents such as antibacterial and antifungal drugs, anti-inflammatory drugs, mitogenic and differentiating agents, etc.

In a similar manner, mutatis mutandis, devices other than membranes, such as tubes can be produced from the collagen matrix.

The collagen devices are then dried and sterilized. For this purpose the collagen devices may be dehydrated either in air or by immersion in alcohol solution (30%–100%). The dehydrated devices may then be subjected to critical point drying, e.g. in carbon dioxide ($CO_2$) or in another gas such as Freon in a critical point dryer, e.t. at about 41° C. and a pressure of about 80–90 bars. It was found that this procedure sterilizes the devices and renders them completely dry, effective to prolong their shelf life. This procedure does not effect the capability of these collagen devices to resist collagenolytic degradation. Furthermore, such a procedure preserves the 3-dimensional shape of the device.

In order to produce a membrane having portions which are degraded at different degradation rates, those parts that are designated to withstand degradation for longer periods of time are brought into contact with the ribose solution. After the required time period the entire membrane is incubated with the ribose solution.

For example, to produce a rectangular membrane with a gradient of degradation rates, having the direction from one short base of the rectangle to the opposite (one short base has a high degradation rate and the other has a low degradation rate), the following procedures may be undertaken:

While the membrane is maintained in a 100% humidified atmosphere, a portion of the rectangular membrane adjacent to one of the two short bases is dipped in the ribose solution for a predetermined time period. Thereafter, adjacent portions are gradually immersed in the ribose solution for predetermined time periods. Thus, the far end will remain the least amount of time in the ribose solution and will thus be the most susceptible portion to degradation.

Space Maintainers (a) Lyophilized hyaluronan

Hyaluronan obtained from human, bovine or avian sources is dissolved in an aqueous solution enriched, or non-enriched with one of the above-mentioned factors and then lyophilized. It was found in accordance with the invention that enriched lyophilized hyaluronan implanted in the skin absorbs water, swells and undertakes a gelatinous consistency, and thus is suitable to serve the purpose of space maintainer.

(b) Bone products or hydroxyapatite product 1 g of mineralized freeze-dried bone, deproteinazed bone, or synthetic hydroxyapatite, are mixed with a solution containing up to 15 mg of osteocalcine and/or 10 mg of vitronectin, and the mixture is then lyophilized.

Particles of demineralized freeze-dried bones are heated at temperatures ranging between 50° C.–100° C. for periods of time ranging between 5 min to 240 min in a dry atmosphere or in a caustic solution. If the heat treatment is done in aqueous solution the demineralized bone is freeze-dried again following the heat treatment. It was found in accordance with the invention that there is a linear correlation between the rate of demineralized bone degradation by trypsin in vitro and the heat temperature.

(c) Use of space maintainers together with collagen

The space maintainers to be used in conjunction with the collagen barrier will consist of each of the above-mentioned materials or of combinations of them. For example, the space maintainer may consist of lyophilized matrix of hyaluronan which comprises particles of heat-treated demineralized freeze-dried bone and/or deproteinazed bone treated with osteocalcine vitronectin. To prepare such a material heat-treated demineralized freeze-dried bone and enriched deproteinazed bone is mixed with a solution of hyaluronan and the mixture is then lyophilized.

EXAMPLE I

In vitro degradation

Collagen fibrils radioactively labelled with tritium, were incubated in a PBS solution either comprising or not comprising ribose. The amount of the collagen fibrils in the solution was 3 µg/ml and the concentration of ribose was 0.2 M. The incubation of the collagen fibrils in the solution was at a temperature of 37° C. and was for periods of time ranging between 1 and 16 days.

Following this incubation, the so-formed collagen matrices were incubated with collagenase (1:10 collagen:collagenase ratio, by weight) for 1, 2 or 4 hours. Following this incubation, the solutions were centrifuged and the amount of radioactivity that remained which consisted of the following collagen matrix, was determined. The results of the radioactive counts are shown in FIG. 1. As can be seen, the radioactivity which remained in the matrix after treatment with collagenase following incubation of the collagen fibrils in PBS ((b) in FIG. 1) less than 40%. Against this, the amount of radioactivity which remained in the matrix formed following incubation in the ribose solution for a period longer than 6 days (FIG. 1) was about 85–90%.

This clearly shows that the collagen matrix formed following incubation in the ribose solution, which brings to cross-linking of the collagen molecules to one another, was highly more resistant to specific degradation by collagenase than the other matrix.

EXAMPLE II

In vivo degradation (a) Collagen matrices, 100 µg each, comprising radiolabelled collagen were treated for 1, 3 and 9 days with ribose in a similar manner to that described in Example 1. The matrices were then implanted in a rat through a standard hole (about 1×3 mm) performed in the femur of the rat. Animals were sacrificed at times 0, 7, 14 and 21 days following implantation and the amount of radioactivity left in each hole was determined. Five animals were sacrificed at each time point.

By measuring the radioactivity and comparing it to the radioactivity existing in the prepared collagen matrix, the degradation rate could be determined. It showed that the preparations degraded at a rate of 3%, 2% and 0.5% per day, for the preparations treated with ribose for 1, 3 and 9 days, respectively.

(b) Membranes prepared as in Example I, having a size of about 0.5×1 cm, were implanted under the gingiva in dogs as well as in humans, following 9 day treatment with ribose as above. Utilizing histological methods it was found that it took about 4 months for complete degradation of the membranes in the dogs. By means of a re-entry procedure performed in the humans, it was determined that it took about six months for complete degradation and disappearance of the membranes. The fact that the membranes are maintained in situ for such long periods of time facilitates their use in guided tissue regeneration.

EXAMPLE III

Animal Experimentation

Collagen membrane prepared as above were used to treat experimental periodontal defects performed on the buccal aspect of dog premolars. Histological examination of the treated sites 4 months after treatment with the collagen membranes revealed 90% regeneration of the defects' size.

We claim:

1. A process for the preparation of a collagen matrix from collagen comprising:
   (i) incubating said collagen with pepsin;
   (ii) dissolving said collagen incubated with pepsin in a solvent;
   (iii) transferring said dissolved collagen to a mold and incubating it to obtain a membrane;
   (iv) compressing said membrane until a desired membrane thickness is obtained;
   (v) reacting said compressed membrane with a reducing sugar under conditions wherein fibrils of the collagen become cross-linked to one another thus forming a matrix; and
   (vi) subjecting said matrix to critical point drying.

2. The process of claim 1 further comprising after step (v) the step of dehydrating said matrix prior to critical point drying.

3. The process of claim 1 wherein said solvent is acetic acid.

4. The process of claim 1 wherein said reducing sugar is a compound presented by one of the following formulae I or II:

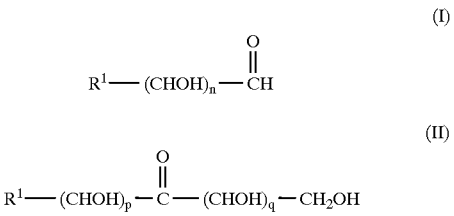

wherein:
   $R^1$ is H or lower alkyl or alkylene, an amino acid, a peptide, a saccharide, purine or pyrimidine base, a phosphorylated purine or pyrimidine base;
   n is an integer between 2–9, and
   p and q are each independently an integer between 0–8, provided that p and q together are at least 2 and not more than 8.

5. A process according to claim 4 wherein the reducing sugar is a diose, triose, tetrose, pertose, hexose, septose, octose, nanose or decose.

6. A process according to claim 5 wherein the reducing sugar is selected from the group consisting of glycerose, threose, erythrose, lyxose, xylose, arabinose, ribose, allose, altrose, glucose, mannose, gulose, idose, galactose and talose.

7. A process according to claim 6 wherein the reducing sugar is ribose.

8. A process according to claim 1 wherein the reducing sugar is enriched with one or more of an antimicrobial agent, an anti-inflammatory agent or a factor having a tissue inductive properties, said agent or factor becoming immobilized within the matrix.

9. A process according to claim 2 wherein said dehydration step is carried out by contacting the matrix with an alcohol solution.

10. A collagen matrix obtained by a process for its preparation from collagen, said process comprising the following steps:
    (i) incubating said collagen with pepsin;
    (ii) dissolving said collagen incubated with pepsin in a solvent;
    (iii) transferring said dissolved collagen to a mold and incubating it to obtain a membrane;
    (iv) compressing said membrane until a desired membrane thickness is obtained;
    (v) reacting said compressed membrane with a reducing sugar under conditions wherein fibrils of the collagen become cross-linked to one another thus forming a matrix; and
    (vi) subjecting said matrix to critical point drying.

11. A collagen matrix according to claim 10 wherein said process further comprises after step (v) the step of dehydrating said matrix prior to critical point drying.

12. The matrix according to claim 11, in the form of an implantable device.

13. The matrix according to claim 12, wherein the device is a collagen based membrane barrier for guided tissue regeneration.

14. The matrix according to claim 10, in the form of an implantable device.

15. The matrix according to claim 14, wherein the device is a collagen based membrane barrier for guided tissue regeneration.

16. A kit for use in guided tissue regeneration, comprising a membrane barrier for guided tissue regeneration and a substance for use as a space maintainer, said membrane barrier being a collagen based membrane barrier of claim 13, said space maintainer being hyaluronic acid.

17. A kit according to claim 16 wherein the space maintainer comprises also an additive being one or more of the group consisting of antimicrobial agents, anti-inflammatory agents and factors having tissue regenerating induction properties.

18. A kit according to claim 16 wherein the space maintainer comprises also substance selected from the group consisting of collagen, fibrin, attachment factors, heparin, sulfate, dermatan sulfate and keratin sulfate.

19. A method for guided tissue regeneration in a site where tissue was destroyed by disease or trauma, comprising implanting within the site the device according to claim 12.

20. A kit according to claim 6 wherein the space maintainer comprises also an additive being one or more of the group consisting of antimicrobial agents, anti-inflammatory agents and factors having tissue regenerating induction properties.

* * * * *

UNITED STATES PATENT AND TRADEMARK OFFICE
CERTIFICATE OF CORRECTION

PATENT NO. : 5,955,438
DATED : Sep. 21, 1999
INVENTOR(S) : Sandu Pitaru et al.

It is certified that error appears in the above-identified patent and that said Letters Patent is hereby corrected as shown below:

Column 9, claim 5, line 47, delete "pertose" and insert therefor --pentose--

Column 10, claim 18, line 46, before "substance" insert --a--; line 48, delete "keratin" and insert therefor --keratan--.

Column 10, claim 20, line 54, delete "6" and insert therefor --14--

Signed and Sealed this

Twenty-ninth Day of May, 2001

Attest:

NICHOLAS P. GODICI

Attesting Officer     Acting Director of the United States Patent and Trademark Office

UNITED STATES PATENT AND TRADEMARK OFFICE
CERTIFICATE OF CORRECTION

PATENT NO. : 5,955,438
DATED : September 21, 1999
INVENTOR(S) : Sandu Pitaru et al.

It is certified that error appears in the above-identified patent and that said Letters Patent is hereby corrected as shown below:

Column 9,
Line 47, delete "pertose" and insert therefor -- pentose --

Column 10,
Line 46, before "substance" insert -- a --
Line 48, delete "keratin" and insert therefor -- keratan --
Line 54, delete "6" and insert therefor -- 14 --

Signed and Sealed this

Twenty-fourth Day of June, 2003

JAMES E. ROGAN
*Director of the United States Patent and Trademark Office*